US008425542B2

(12) United States Patent
Moftakhar et al.

(10) Patent No.: US 8,425,542 B2
(45) Date of Patent: *Apr. 23, 2013

(54) ANEURYSM OCCLUSION DEVICE CONTAINING BIOACTIVE AND BIOCOMPATIBLE COPOLYMER SHELL AND BIOCOMPATIBLE METALLIC FRAME MEMBER

(75) Inventors: Roham Moftakhar, Madison, WI (US); Kristyn S. Masters, Madison, WI (US); Wendy C. Crone, Madison, WI (US); Fangmin Xu, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 878 days.

This patent is subject to a terminal disclaimer.

(21) Appl. No.: 12/110,094

(22) Filed: Apr. 25, 2008

(65) Prior Publication Data
US 2009/0062834 A1 Mar. 5, 2009

Related U.S. Application Data

(60) Provisional application No. 60/926,449, filed on Apr. 27, 2007, provisional application No. 60/926,979, filed on Apr. 27, 2007.

(51) Int. Cl.
*A61B 17/08* (2006.01)
(52) U.S. Cl.
USPC .................. 606/158; 606/200; 527/300
(58) Field of Classification Search .................. 606/151, 606/157, 158, 200; 424/423; 527/300
See application file for complete search history.

(56) References Cited

U.S. PATENT DOCUMENTS

| 4,500,676 | A | 2/1985 | Balazs et al. |
| 5,202,431 | A | 4/1993 | della Valle et al. |
| 5,342,348 | A | 8/1994 | Kaplan |
| 5,545,213 | A | 8/1996 | Keogh et al. |
| 6,107,416 | A | 8/2000 | Patnaik et al. |
| 6,197,051 | B1 | 3/2001 | Zhong |
| 6,335,384 | B1 | 1/2002 | Evans et al. |
| 6,346,117 | B1 | 2/2002 | Greenhalgh |
| 6,364,823 | B1 | 4/2002 | Garibaldi et al. |

(Continued)

FOREIGN PATENT DOCUMENTS

| EP | 0184465 A | 6/1986 |
| EP | 0184465 A2 | 6/1986 |

(Continued)

OTHER PUBLICATIONS

Office action from U.S. Appl. No. 12/110,096, dated Oct. 15, 2010.

(Continued)

*Primary Examiner* — Corrine M McDermott
*Assistant Examiner* — Alexander Orkin
(74) *Attorney, Agent, or Firm* — Armstrong Teasdale LLP

(57) ABSTRACT

An endovascular device for occluding a vascular aneurysm is disclosed. The device includes a polymeric shell member that, in one embodiment, may be constructed from a bioactive and biocompatible polyurethane-diol-glycosaminoglycan copolymer, and a biocompatible metallic frame member. The copolymer is sufficiently flexible and strong for endovascular delivery into a vascular aneurysm and for use as a polymeric shell for receiving the biocompatible metallic frame member. The biometallic frame member may include one or more components constructed from a NiTi alloy.

25 Claims, 10 Drawing Sheets

U.S. PATENT DOCUMENTS

| | | | |
|---|---|---|---|
| 6,376,742 B1 * | 4/2002 | Zdrahala et al. | 623/11.11 |
| 6,579,978 B1 | 6/2003 | Renier et al. | |
| 7,045,585 B2 | 5/2006 | Berry et al. | |
| 7,201,918 B2 | 4/2007 | Cruise | |
| 7,481,821 B2 * | 1/2009 | Fogarty et al. | 606/194 |
| 7,744,652 B2 * | 6/2010 | Morsi | 623/23.72 |
| 2002/0165572 A1 | 11/2002 | Saadat | |
| 2003/0220666 A1 * | 11/2003 | Mirigian et al. | 606/200 |
| 2003/0225391 A1 | 12/2003 | Cragg et al. | |
| 2004/0102805 A1 | 5/2004 | Cheng et al. | |
| 2004/0110722 A1 | 6/2004 | Ornberg et al. | |
| 2004/0225279 A1 | 11/2004 | Raymond | |
| 2005/0158272 A1 | 7/2005 | Whirley et al. | |
| 2005/0238716 A1 | 10/2005 | Verrijk et al. | |
| 2005/0267510 A1 | 12/2005 | Razack | |
| 2006/0052816 A1 * | 3/2006 | Bates et al. | 606/200 |
| 2006/0089710 A1 | 4/2006 | Ornberg et al. | |

FOREIGN PATENT DOCUMENTS

| | | | |
|---|---|---|---|
| WO | 98/45335 A1 | 10/1998 | |
| WO | WO9845335 A | 10/1998 | |
| WO | 0128434 A1 | 4/2001 | |
| WO | 2004039422 A1 | 5/2004 | |
| WO | 2006000763 A2 | 1/2006 | |
| WO | 2007016251 A2 | 2/2007 | |

OTHER PUBLICATIONS

Invitation to Pay Additional Fees from PCT/US2008/061503, dated Apr. 16, 2009.

Non-final Office Action for U.S. Appl. No. 12/110,096 mailed Apr. 16, 2009.

Office action from U.S. Appl. No. 12/110,096 dated, Mar. 31, 2010.

International Search Report and Written Opinion for PCT/US2008/061503 mailed Jun. 29, 2009.

Kwan, Kwon, and Borden, "Successful Thrombolysis in the Vertebrobasilar Artery after Endovascular Occlusion of a Recently Ruptured Large Basilar Tip Aneurysm," Apr. 16, 1995, pp. 847-851.

International Search Report and Written Opinion for PCT/US2008/061492 mailed Jul. 24, 2008.

Broderick, JP, et al., "Intracerebral hemorrhage more than twice as common as subarachnoid hemorrhage," J. Neurosurg., vol. 78, p. 188-191, Feb. 1993.

Cognard, C., et al., "Long-term Angiographic Follow-up of 169 Intracranial Berry Aneurysms Occluded with Detachable Coils," Radiology, vol. 212, No. 2, pp. 348-356, Aug. 1999.

Duerig, T.W., et al., "Superelastic Nitinol for Medical Devices," Medical Plastics and Biomaterials Magazine, 1997, pp. 30-43.

Freiherr, G., "The Light Stuff: Optical Imaging in Medical Diagnosis," Medical Device and Diagnostic Industry Magazine, Jun. 1998, pp. 52-59.

Kuo and Ma, "Ionically crosslinked alginate hydrogels as scaffolds for tissue engineering: Part 1. Structure, gelation rate and mechanical properties," Biomaterials, 2001, vol. 22, pp. 511-521.

Leach, JB, et al., "Hyaluronan" in Encyclopedia of Biomaterials and Biomedical Engineering, Wnek GE, et al., eds., Marcel Dekker, New York, 2004, pp. 779-789.

Linhardt, RJ, et al., "Isolation and characterization of human heparin," Biochemistry, 1992, vol. 31(49), pp. 12441-12445.

Otsuka and Wayman, eds., "Shape Memory Materials," Cambridge University Press, 1998, pp. 49-96, 133-143, and 267-281.

Schmitz-Rode, T., et al., "Embolotherapy of Aneurysms Under Temporary Balloon Occlusion of the Neck, In Vitro Study of a Newly Designed Eccentric Balloon Catheter," Investigative Radiology, 1999, vol. 34(4), pp. 317-321.

Shabalovskaya, SA, "Biological Aspects of TiNi Alloy Surfaces," Journal de Physique IV, 1995, C8-1199.

Tiwari, A., et al., "New prostheses for use in bypass grafts with special emphasis on polyurethanes," Cardiovascular Surgery (London, England), vol. 10, No. 3, pp. 191-197 (2002).

Xu, et al., "The haemocompatibility of polyurethane-hyaluronic acid copolymers," Biomaterials, vol. 29, p. 150-160, 2008.

Official Letter from the European Patent Office dated Jan. 25, 2012.

Office action from U.S. Appl. No. 12/110,096, dated Feb. 17, 2012.

* cited by examiner

ANEURYSM OCCLUSION DEVICE CONTAINING BIOACTIVE AND BIOCOMPATIBLE COPOLYMER SHELL AND BIOCOMPATIBLE METALLIC FRAME MEMBER

CROSS REFERENCE TO RELATED APPLICATIONS

This patent application claims priority to U.S. Provisional Patent Application Ser. Nos. 60/926,449 and 60/926,979, both of which were filed on Apr. 27, 2007, the entirety of each is hereby incorporated by reference.

STATEMENT REGARDING FEDERALLY SPONSORED RESEARCH OR DEVELOPMENT

This invention was made with United States government support awarded by the following agencies:
NIH EB005440
NSF 0134385
USAF/AFOSR FA9550-04-1-0109
The United States government has certain rights in this invention.

STATEMENT REGARDING FEDERALLY SPONSORED RESEARCH OR DEVELOPMENT

This invention was made with United States government support awarded by the following agencies: NSF 0134385 and USAF/AFOSR FA9550-04-1-0109. The United States has certain rights in this invention.

BACKGROUND OF THE INVENTION

The present disclosure is directed to an endovascular aneurysm occlusion device and methods for occluding aneurysms. More particularly, the present disclosure is directed to an endovascular aneurysm occlusion device that includes a biocompatible polymeric member and a biocompatible metallic frame member. In one exemplary method for occluding a cerebral aneurysm, the biocompatible polymeric member is introduced into the aneurysm and then the biocompatible metallic frame member is introduced into the polymeric member to expand the device to the shape of the aneurysm. Device placement leads to biological isolation of the aneurysm and initiates a cascade of wound healing events at the aneurysm site that provides for improved patient outcomes.

Cerebral aneurysms may form due to damage to the internal elastic lamina of blood vessels by hemodynamic factors. Weakening of the vessel wall leads to formation of a bulge known as an aneurysm. As many as 5 million individuals in North America may harbor cerebral aneurysms. (Broderick J P et al., *J Neurosurg* 78, 188 (February 1993)). Cerebral aneurysms are at risk of rupture, which is referred to as subarachnoid hemorrhage (SAH). SAH is a devastating condition with high morbidity and mortality. In the U.S., SAH is associated with an annual cost of $1.75 billion. To avoid further complications, un-ruptured and ruptured aneurysms need to be treated. Immediate and long-term obliteration of the aneurysm is important to prevent subsequent growth and rupture.

The majority of cerebral aneurysms are currently treated from inside of the blood vessel, which is referred to as the endovascular route. Endovascular devices used to occlude aneurysms include coils (very common), intravascular injections, and detachable intravascular balloons. During coil embolization (or, "coiling"), metal components made from platinum (Pt) or nickel titanium (NiTi) are threaded through a catheter and deployed into the aneurysm. A primary goal of the operation is to densely fill the aneurysm cavity with coil loops, which block blood flow into the aneurysm and prevent rupture. The aneurysm is blocked by interlaced coils, which gradually form a collagen membrane isolating the aneurysm from circulation. Use of these coils is accompanied by numerous complications, however.

One significant drawback with known coiling occlusion devices is coil compaction over time which leads to incomplete aneurysm occlusion in approximately 30% of cases. (Cognard C et al., *Radiology* 212, 348 (August 1999)). Such incomplete occlusion causes aneurysm enlargement and subsequent rupture. Another significant drawback associated with known occlusion coils is blood clotting in the aneurysm. Yet another drawback associated with known occlusion coil treatments is unpredictability of aneurysm healing. Still another drawback of known aneurysm treatments is imprecise placement of numerous coils into the aneurysm, one by one, until the entire aneurysm is filled. Larger sized aneurysms require time-consuming placement of many coils, which leads to increased risk of morbidity and mortality while the patient is under general anesthesia. Placement of each individual coil into the aneurysm is also a procedural risk, which increases morbidity and mortality of the procedure.

Another approach that has been utilized to treat cerebral aneurysms includes filling the aneurysm with a liquid embolic agent and allowing the liquid embolic agent to harden over time (generally through crosslinking when contacted with blood) and occlude the aneurysm. This method, however, has numerous shortcomings including the lack of any containment mechanism for the liquid embolic agent once injected into the aneurysm. It has been found that lack of containment of the liquid embolic agent can result in leakage into normal circulation prior to solidification. This leakage can ultimately lead to blood vessel occlusion and stroke. Further, the lack of containment can also result in incomplete filling of the aneurysm and a decrease in effectiveness of the treatment. Additionally, when this approach has been utilized there have been reports of problems filling the vascular defects with the embolic liquid as the leading surface of the embolic liquid being injected into the aneurysm reacts and hardens thus making complete injection into the aneurysm very difficult.

Polyurethane copolymers have been widely used for numerous biomedical applications due to their excellent mechanical properties, biocompatibility, and hemocompatibility. In contrast to other materials used in vascular applications, such as polytetrafluoroethylene (PTFE) and polyethylene terephthalate (PET), polyurethane-based materials support the growth of endothelial cells and possess mechanical properties that match the native vasculature. (Tiwari A et al., *Cardiovascular surgery* (London, England) 10, 191 (2002).

Surface and/or bulk modification of polyurethane may be accomplished, such as by attaching biologically active species to reactive groups on the polyurethane molecule. Such modifications may be designed to control/mediate host wound healing responses. However, polyurethane is not inherently bioactive.

Hyaluronic acid (HA) and heparin are glycosaminoglycans (GAGs) found in all mammals. Hyaluronic acid is a unique and highly versatile biopolymer. Hyaluronic acid plays a vital role in embryonic development, extracellular matrix homeostasis, wound healing, and tissue regeneration. However, the exact mechanisms of hyaluronic acid's regulation of these events are unknown. The behavior and cell influences of hyaluronic acid are highly dependent upon its concentration and molecular weight. Biomaterials made from derivatized and cross-linked hyaluronic acid have been reported in the bioengineering community for applications such as orthopedic, cardiovascular, opthalmology, dermatology, and general applications in tissue engineering, surgery and drug delivery. Hyaluronic acid is naturally derived and nonimmunogenic. It also has multiple sites for modification and inherent biological activities. (Leach J B et al., *Encyclopedia of Biomaterials and Biomedical Engineering* 2004, p. 779).

SUMMARY OF THE INVENTION

One aspect of the invention is an endovascular medical device comprising a polymeric member defining an interior chamber and constructed from a copolymer comprising the reaction product of a biocompatible urethane and a bioactive polysaccharide, and, a biocompatible metallic frame member comprising one or more wires constructed from a NiTi alloy having a transformation temperature below a patient's body temperature, disposed within the interior chamber, and adapted to structurally support the polymeric member. Use of "frame" is intended to refer to the functional aspect of providing structural framework and support, and not necessarily to any particular form, shape, geometry or the like. "Bioactive" refers to molecules that actively participate in events related to native biological regulation or function, such as molecules that inhibit platelet adhesion and/or support appropriate cellular activity. "Biocompatible" refers to molecules that provide structural and mechanical properties in physiological environments without eliciting any material undesirable effects in cells or without inducing any material undesirable local or systemic responses in the host, such as uncontrolled activation of immunogenic or thrombotic cascades. The weight content of the cetylpyridinium salt of hyaluronic acid is an amount sufficient to render the copolymer bioactive. Preferably, the weight content of the polyurethane-diol is an amount sufficient to render the copolymer sufficiently flexible and rigid for endovascular delivery into a vascular aneurysm and for use as a polymeric shell, having coiled NiTi component, such as a coiled wire, disposed therein, within the vascular aneurysm.

Another aspect of the present invention is an endovascular medical device comprising a polymeric member defining an interior chamber and a liquid embolic agent. The liquid embolic agent is capable of solidifying inside of the polymeric member upon activation.

Another aspect of the present invention is an endovascular medical device comprising a polymeric member defining an interior chamber and a liquid embolic agent including a first component and a second component. The first component and the second component that comprise the liquid embolic agent are capable of solidifying inside of the polymeric member upon mixing together.

Another aspect of the present invention is a method of occluding a vascular aneurysm comprising endovascularly disposing into a vascular aneurysm an elastic hemocompatible polymeric member defining an interior chamber and endovascularly disposing a liquid embolic agent within the interior chamber. The liquid embolic agent is then activated to solidify the liquid embolic agent in the chamber.

Another aspect of the present invention is a method of occluding a vascular aneurysm comprising endovascularly disposing into a vascular aneurysm an elastic hemocompatible polymeric member defining an interior chamber and endovascularly disposing a liquid embolic agent including a first component and a second component within the interior chamber and allowing the first and second component to mix together and solidify.

In an exemplary embodiment of the medical device, the bioactive polysaccharide is a bioactive glycosaminoglycan.

In another exemplary embodiment of the medical device, the bioactive glycosaminoglycan is a suitable salt of hyaluronic acid or a suitable salt of heparin, or dermatan sulfate, which includes such salts that are sufficiently soluble in dimethylformamide (DMF) or tetrahydrofuran (THF) to react with the other reactants as set forth in the chemical synthesis at FIGS. 5 and 6 and provide the copolymer end-product, or those set forth in Xu et al. (*Biomaterials* 29: 150-160, 2008).

In another exemplary embodiment of the medical device, the salt of hyaluronic acid is a cetylpyridinium salt or a tetrabutylammonium salt, and the salt of heparin is a dimethyldioctadecylammonium salt.

In another exemplary embodiment of the medical device, the salt of hyaluronic acid has 5 to 10,000 repeating units, and the dimethyldioctadecylammonium salt of heparin has 5 to 65 repeating units, and the dimethyldioctadecylammonium salt of dermatan sulfate has 5 to 50 repeating units.

In another exemplary embodiment of the medical device, the weight content of the bioactive polysaccharide is in the range of about 0.05% to about 30%.

In another exemplary embodiment of the medical device, the high and low range endpoints of the weight content of the bioactive polysaccharide are any combination of 0.05%, 0.1%, 0.33%, 0.66%, 1.3%, 2.0%, 5.4%, 10% and 30%.

In another exemplary embodiment of the medical device, the cetylpyridinium salt of hyaluronic acid is employed.

In another exemplary embodiment of the medical device, the biocompatible urethane is the reaction product of 4,4'-methylene-di-(p-phenyl isocyanate) and poly(tetramethylene oxide)$_n$ and further reacted with 1,4-butanediol. Preferably, n=10 to 40.

In another exemplary embodiment of the medical device, the biocompatible urethane is the reaction product of 4,4'-methylene-di-(p-phenyl isocyanate) and poly(tetramethylene oxide), and further reacted with 1,4-butanediol. Preferably, n=10 to 40.

In another exemplary embodiment of the medical device, the biocompatible urethane is the reaction product of a suitable isocyanate-containing molecule and a suitable poly($C_{2-10}$ alkylene oxide)$_n$ and further reacted with a suitable $C_{4-50}$ diol-containing molecule, wherein n=10 to 40, wherein the $C_{2-10}$ alkylene is linear or branched, substituted or un-substituted, and wherein the $C_{4-50}$ is linear or branched, substituted or un-substituted. Such suitable isocyanate-containing molecules, poly($C_{2-10}$ alkylene oxide), molecules, and the $C_{4-50}$ diol-containing molecules are sufficiently soluble in DMF or THF to react and provide the end product copolymer as set forth in FIGS. 5 and 6.

In another exemplary embodiment of the medical device, the polymeric member has a wall thickness in the range of 0.05 to 0.4 mm.

In another exemplary embodiment of the medical device, the polymeric member is adapted to substantially conform to a vascular aneurysm.

In another exemplary embodiment of the medical device, the alloy comprises in the range of about 49 to about 51 wt. % Ni and in the range of about 51 to about 49 wt. % Ti, whereby trace amounts of Cu, Fe and Al may also be present. ("Shape Memory Materials," K. Otsuka and C M Wayman, Editors, Cambridge University Press, 1998).

In another exemplary embodiment of the medical device, the metallic frame member comprises a single component.

In another exemplary embodiment of the medical device, the metallic frame member is in the shape of a coil.

Another aspect of the invention is an endovascular method of occluding a vascular aneurysm comprising the steps or acts of endovascularly disposing into a vascular aneurysm an elastic hemocompatible polymeric member defining an interior chamber, and, endovascularly disposing a biocompatible metallic frame member within the interior chamber.

In an exemplary embodiment of the endovascular method, the metallic frame member comprises one or more components constructed from a biocompatible NiTi alloy having a transformation temperature below a patient's body temperature, and the polymeric member is constructed from a copolymer comprising the reaction product of a biocompatible urethane and a bioactive glycosaminoglycan, the method further comprising the steps or acts of endovascularly threading the NiTi component through a catheter, threading the NiTi component into the interior chamber, and, allowing the NiTi component to expand to its predetermined shape within the interior chamber, taking the form of the frame adapted to structurally support the polymeric member.

In another exemplary embodiment of the method, the biocompatible urethane is the reaction product of 4,4'-methylene-di-(p-phenyl isocyanate) and poly(tetramethylene oxide)$_n$ and further reacted with 1,4-butanediol, wherein n=10 to 40.

In an exemplary embodiment of the method, the biocompatible urethane is the reaction product of a suitable isocyanate-containing molecule and a suitable poly($C_{2-10}$ alkylene oxide), and further reacted with a suitable $C_{4-50}$ diol-containing molecule, wherein n=10 to 40, wherein the $C_{2-10}$ alkylene is linear or branched, substituted or un-substituted, and wherein the $C_{4-50}$ is linear or branched, substituted or un-substituted.

In another exemplary embodiment of the method, the glycosaminoglycan is a cetylpyridinium salt of hyaluronic acid having 5 to 10,000 repeating units, a tetrabutylammonium salt of hyaluronic acid having 5 to 10,000 repeating units, or a dimethyldioctadecylammonium salt of heparin having 5 to 65 repeating units, or a dimethyldioctadecylammonium salt of dermatan sulfate having 5 to 50 repeating units.

In another exemplary embodiment of the method, the weight content of the glycosaminoglycan is in the range of about 0.05% to about 30%.

In another exemplary embodiment of the method, the high and low range endpoints of the weight content of the bioactive polysaccharide are any combination of 0.05%, 0.1%, 0.33%, 0.66%, 1.3%, 2.0%, 5.4%, 10% and 30%.

In another exemplary embodiment, the method further comprises the steps or acts of substantially conforming the polymeric member to the vascular aneurysm, and contacting a substantial portion of the metallic frame member with the polymeric member.

Another aspect of the invention is an endovascular device for occluding a vascular aneurysm comprising a polymeric member defining an interior chamber and constructed from an elastic, hemocompatible polymer, and, a biocompatible metallic frame member comprising one or more components constructed from a NiTi alloy having a transformation temperature below a patient's body temperature, disposed within the interior chamber, and adapted to structurally support the polymeric member.

Another aspect of the invention is an endovascular medical device comprising a polymeric member defining an interior chamber and constructed from an elastic, hemocompatible polymer, and, a biocompatible metallic frame member comprising one or more components constructed from a NiTi alloy having a transformation temperature below a patient's body temperature, disposed within the interior chamber, and adapted to structurally support the polymeric member. The term "elastic" as used here refers to polymers having greater than 200% elongation in tensile testing without breakage. "Hemocompatible" polymers refers to a subset of biocompatible polymers that further permit contact with blood without inducing adverse or thrombotic reactions. For example, a hemocompatible polymer does not do any of the following: activate platelets or other blood components concerning the coagulation or fibrinolytic pathways; induce formation of thrombi; or, injure circulating blood cells resulting in anemia, hemolysis or other altered blood cell functioning.

In an exemplary embodiment of the medical device, the hemocompatible polymer is poly(ethylene glycol), poly(vinyl alcohol), polytetrafluoroethylene, polyethylene terephthalate, poly(hydroxyethyl methacrylate), poly(hydroxyethyl acrylate), a copolymer thereof, or a anti-thrombotic modified derivative thereof.

In another exemplary embodiment of the medical device, the copolymer is poly(ethylene glycol) diacrylate, poly(ethylene glycol) dimethacrylate or acrylated poly(vinyl alcohol).

In another exemplary embodiment of the medical device, the anti-thrombotic modified derivative includes the hemocompatible polymer modified by an anti-thrombotic agent being heparin, chitosan, or a nitric oxide donor molecule.

In another exemplary embodiment of the medical device, the anti-thrombotic modified derivative is heparin-releasing polyvinylpyrrolidone, heparin-releasing methacrylate, heparin-releasing polyester, nitric oxide-releasing polyester, or nitric oxide-releasing polyvinyl chloride.

In another exemplary embodiment of the medical device, the polymeric member has a wall thickness in the range of 0.05 to 0.4 mm.

In another exemplary embodiment of the medical device, the NiTi component has a thickness in the range of about 0.0047 in to about 0.150 in, preferably about 0.010 in.

In another exemplary embodiment of the medical device, the polymeric member is adapted to substantially conform to a vascular aneurysm.

In another exemplary embodiment of the medical device, the alloy comprises in the range of about 49 to about 51 wt. % Ni and in the range of about 51 to about 49 wt. % Ti.

In another exemplary embodiment of the medical device, the metallic frame member comprises a single component.

In another exemplary embodiment of the medical device, the metallic frame member is in the shape of a coil.

In another exemplary embodiment of the medical device, the liquid embolic agent is a one component liquid embolic agent selected from the group consisting of cyanoacrylate solutions, polyvinyl alcohol solutions, ethylene vinyl copolymer solutions, cellulose acetate solutions, polymethylmethacrylate solutions, polyvinyl acetate solutions, hydrogel solutions, polyurethane solutions, poly(ethylene glycol) solutions, polyester solutions, polyhydroxyethyl methacrylate solutions, polyanhydride solutions, silicone solutions, polysilane solutions and combinations and copolymers thereof.

In another exemplary embodiment of the medical device, the liquid embolic agent comprises a first component selected from a calcium solution and a sodium solution and a second component comprising an alginate solution.

BRIEF DESCRIPTION OF DRAWINGS OF EXEMPLARY EMBODIMENTS

DETAILED DESCRIPTION OF THE EXEMPLARY EMBODIMENTS

Figure 1:
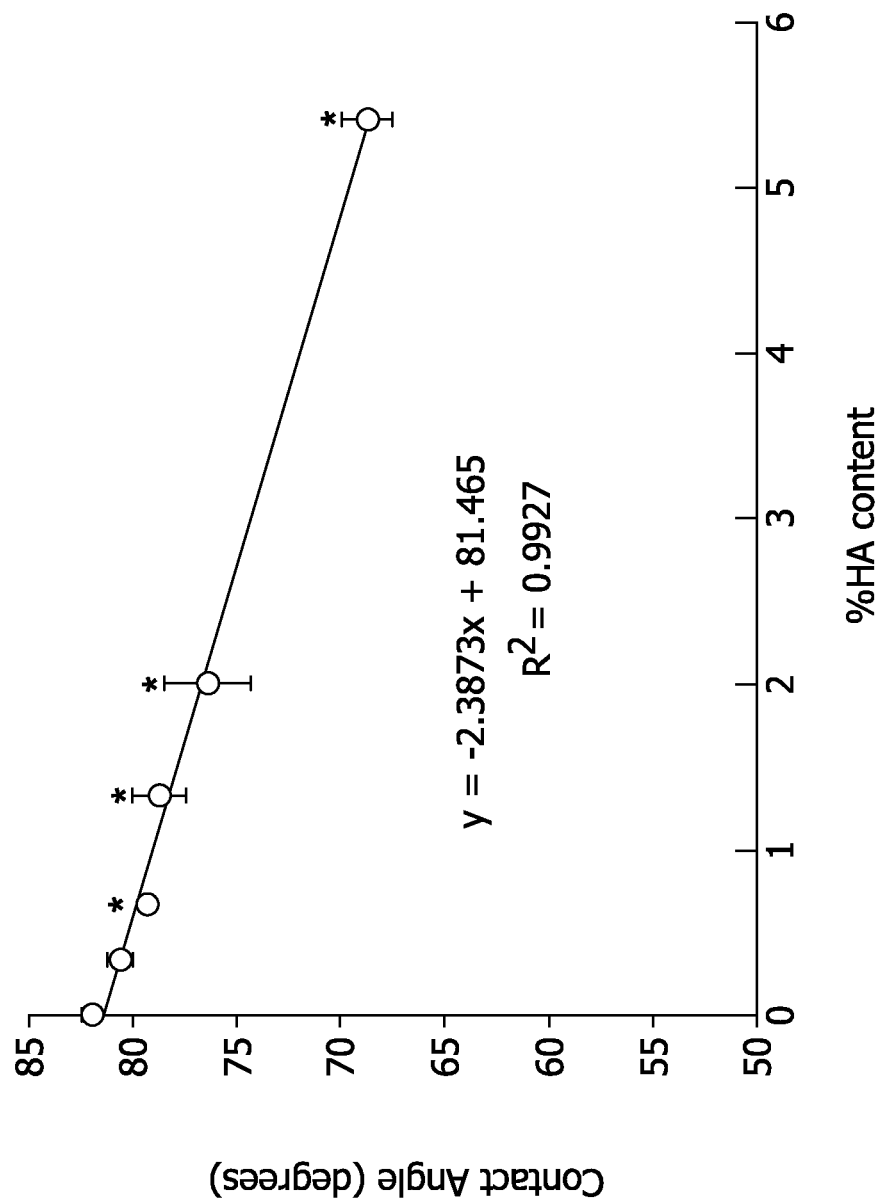
FIG. 1 is a line graph illustrating the contact angle of $diH_2O$ on PUBD-HA copolymer films of varying hyaluronic acid content, whereby hydrophilicity increases with increasing hyaluronic acid content, and whereby the control 1,4-butanediol polyurethane (PUBD) polymer is shown.
Figure 2:
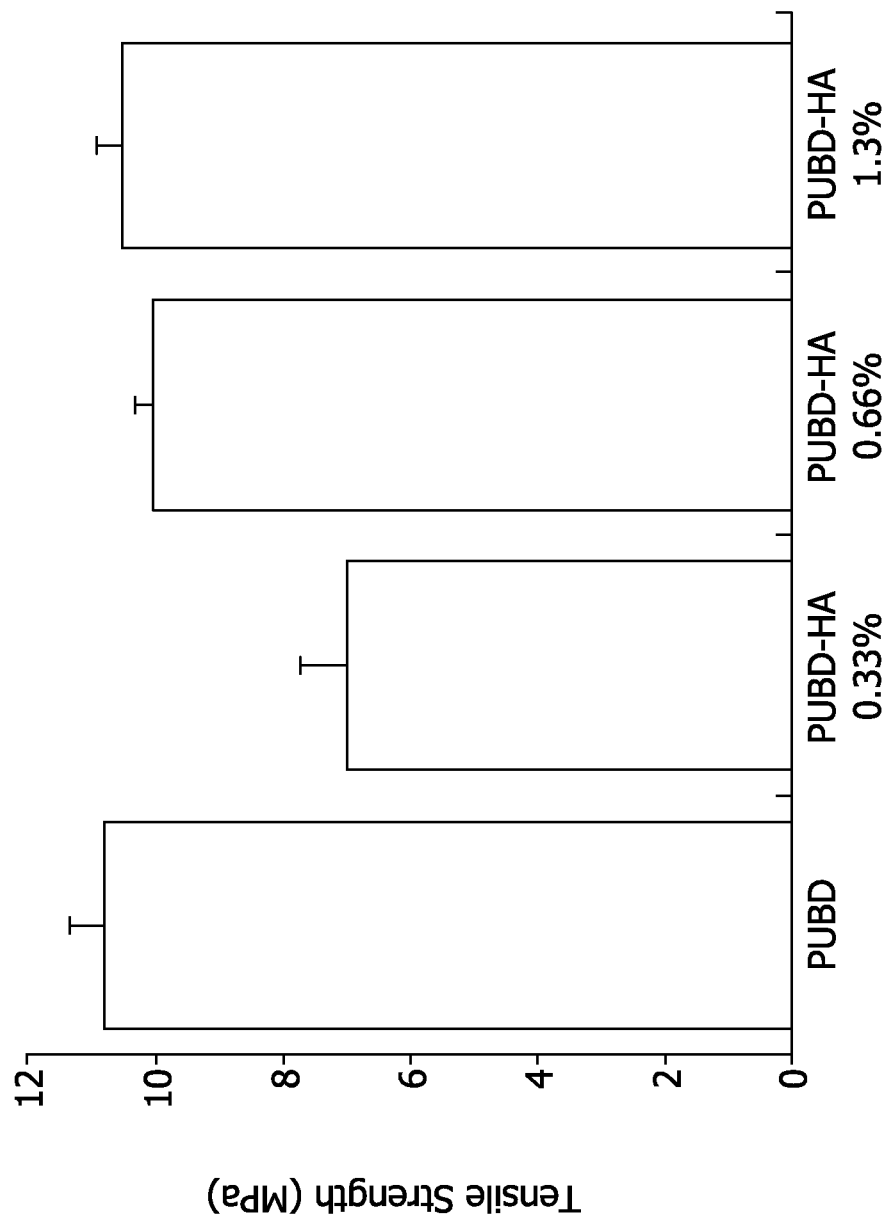
FIG. 2 is a bar graph illustrating tensile strength of PUBD-HA copolymer films of varying hyaluronic acid content compared to the PUBD control.
Figure 3:
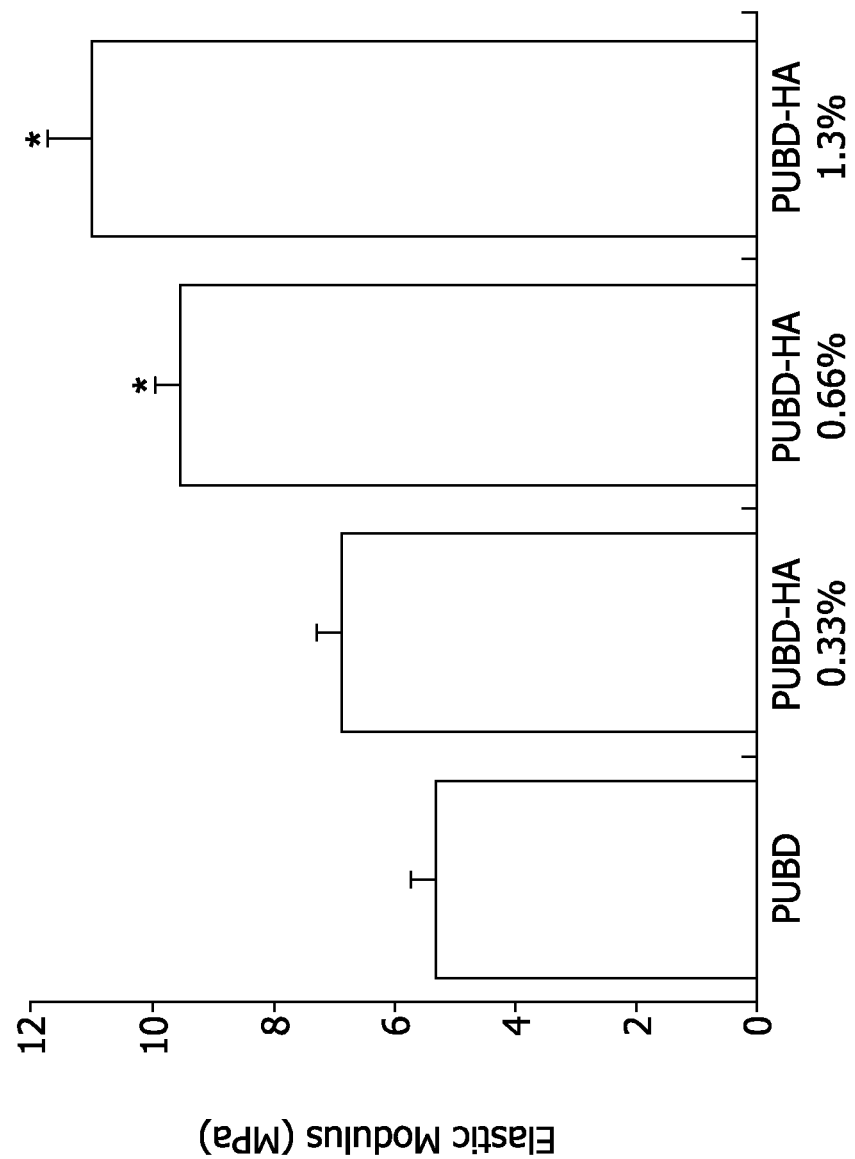
FIG. 3 is a bar graph illustrating elastic modulus of PUBD-HA copolymer films of varying hyaluronic acid content compared to the PUBD control.
Figure 4:
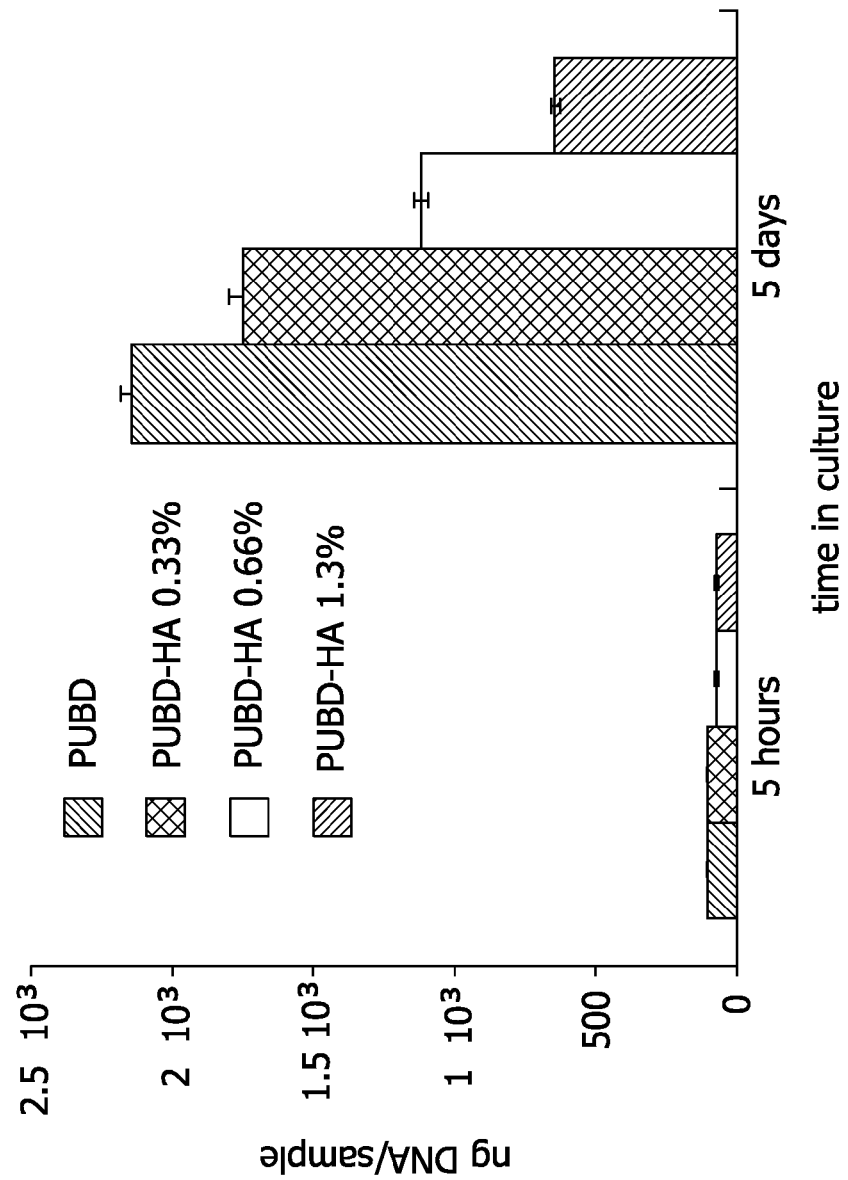
FIG. 4 is a bar graph illustrating fibroblast adhesion and proliferation of PUBD-HA copolymer films of varying hyaluronic acid content compared to the PUBD control.

In one embodiment, the aneurysm occlusion device includes a single nickel titanium (NiTi) component frame surrounded by a polymeric shell that stimulates natural wound healing processes. The NiTi shape memory component is deployed into the polymeric shell, which causes the device to fill the aneurysm resulting in intimate contact between the component stent and surrounding tissue. The bioactive polymer shell initiates a cascade of wound healing events at the aneurysm site that provides biological isolation of the aneurysm, which improves patient outcome. The instant occlusion device advantageously provides more precise and controlled methods of treating aneurysms as compared to existing treatment methods and devices. This instant occlusion device provides several advantages over existing treatment options. It may also eliminate some of the numerous problems associated with coiling and improve patient outcomes.

In another embodiment, the aneurysm occlusion device includes a liquid embolic agent and a polymeric shell that stimulates natural wound healing. Upon use, the device is capable of inserting the polymeric shell into an aneurysm and then filling the polymeric shell with the liquid embolic agent. The liquid embolic agent solidifies within the polymeric shell upon activation and results in intimate contact between the polymeric shell and the surrounding tissue such that a cascade of wound healing events is initiated. As used herein, the term "solidifies," and variants thereof used to describe one state of the embolic agent, means hardened or crosslinked; that is, "solidifies" means that the embolic agent is no longer in the liquid state. Solidification is intended to include various means of transforming from a liquid to a hardened material including, for example, gelling and crosslinking. The term "activation" and variants thereof means initiating a chemical or other reaction to cause the liquid embolic agent to solidify.

The aneurysm occlusion device including a liquid embolic agent and a polymeric shell provides a number of significant advantages over conventional devices. The device, and methods utilizing the device, can result in decreased procedure time such that the patient is under general anesthesia for a shorter period of time. This can reduce the mortality rate associated with anesthesia, and is generally beneficial for patients. Additionally, the aneurysm occlusion device including the liquid embolic agent can provide a patient with an option that has reduced compaction in the aneurysm over time thereby reducing the risks of aneurysm enlargement and subsequent rupture; that is, it can provide the patient an option where the polymeric member mass is not significantly reduced over time.

Another advantage of the aneurysm occlusion device including a liquid embolic agent is that it overcomes the potentially dangerous leakage problems associated with the use of liquid embolic agents alone without any containment mechanism within the aneurysm. This containment mechanism will also facilitate a more precise delivery (both amount and location) of the liquid embolic agent into the aneurysm. A further advantage of the device described herein and including the liquid embolic agent is that it enables the use of a greater variety of liquid embolic agents; that is, to date liquid embolic agents have been limited to those that will form a gelatinous material upon contact with blood. But because the liquid embolic agents used with the aneurysm occlusion device as described herein are injected into a polymeric shell material within the aneurysm and do not directly contact blood, the liquid embolic agents are not required to form a gelatinous material in contact with blood. Because this restriction has been removed, a greater number of liquid embolic agents can be safely and effectively utilized.

The instant polymeric shell overcomes the aforementioned compaction, blood clotting and healing unpredictability problems associated with known coiling occlusion devices. The instant polymeric shell also provides a blood-flow barrier into the aneurysm neck and sac. The instant occlusion device improves patient outcome by decreasing the rate of aneurysm growth, recurrence and rupture.

The bioactive property of the instant polymeric shell provides an environment that stimulates accelerated and optimal healing of the aneurysm, which further decreases the risk of incomplete healing and rupture.

The instant occlusion device is less time-consuming to place into an aneurysm than known occlusion devices, which decreases procedural time, morbidity and mortality, accordingly.

The instant occlusion device includes NiTi shape memory component disposed within a polymeric shell. The NiTi shape memory component provides a structural frame. The component is deployed into the polymeric shell causing the device to fill the aneurysm resulting in intimate contact between the device and surrounding tissue. NiTi is an alloy having shape memory properties as well as biocompatibility and unique properties that facilitate minimally invasive delivery of the occlusion device. The NiTi component has a thickness in the range of about 0.0047 in to about 0.150 in, preferably about 0.010 in.

Shape memory alloys (SMA) such as NiTi constitute a unique class of materials having wide-ranging applications. NiTi alloy is a commercially successful SMA, and it is being used in numerous biomedical, aerospace, automotive and other applications. Of the available SMA materials, NiTi is the only material having suitable biocompatibility, and it has been used in a variety of FDA-approved devices. (Duerig T W et al., *Medical Plastics and Biomaterials Magazine* 1997, 30-43). The biocompatibility characteristics of NiTi are similar to stainless steel in vivo and cobalt-chromium alloys in vitro. (Shabalovskaya S A, *Journal de Physique IV* 1995, C8, 1199). Other properties and advantages of NiTi include exceptional wear and corrosion resistance.

SMA materials undergo reversible phase transformation that provides dramatic and recoverable stress-induced and temperature-induced transformations. The behavior of NiTi SMA is governed by a phase transformation between austenite and martensite crystal structures. Such phase transformation is produced by temperature cycling between the high temperature austenite phase and the low temperature martensite phase (referred to as shape memory effect) by loading the material to favor the high strain martensite phase or unloading to favor the low strain austenite phase (super-elasticity). Preferably, the transformation temperature is set below body temperature so that the NiTi is in austenite form after deployment into the polymeric shell. Such transformation temperature allows the device to have super-elastic capabilities in the body, which also provides device capacity to fill the aneurysm.

The unique mechanical properties associated with SMA materials provide advantages. (Freiherr G, *Medical Device and Diagnostic Industry Magazine* 1998, 52-59). NiTi enables the occlusion device to be collapsed into a catheter without permanently deforming the device. The instant occlusion device is transported to the implantation site in a compact form, which provides for precise positioning. Once ejected from the catheter, the SMA material self-expands to provide a mechanical superstructure. NiTi provides sufficient rigidity to maintain vessel patency. NiTi also provides radial forces low enough to avoid tissue ischemia and necrosis. The instant occlusion device may also be appropriately sized to prevent the possibility of over-expansion which could rupture the aneurysm.

The NiTi component is heat treated to impart a looped shape and a transformation temperature below the body temperature. The component is cooled below its transformation temperature and enclosed inside a catheter in straight form. Deformation is facilitated by warming the component above its transformation temperature. Because the transformation temperature is below the body temperature, the component naturally expands to its open form once ejected from the catheter. The component is ejected into the polymeric shell, which is sized to conform to the aneurysm. The materials have proven biocompatibility. Upon being released from the constraints and thermal insulation of the catheter, the NiTi component deforms within the aneurysm as it is heated above the transformation temperature by the higher body temperature. Upon deformation within the aneurysm, the NiTi component takes the form of a predetermined metallic frame that structurally supports the polymeric shell.

Hyaluronic acid (also referred to as hyaluronan and hyaluronate) is a suitable molecule for enhancing tissue wound healing response upon in vivo implantation. Hyaluronic acid is a polysaccharide naturally present during wound healing. Hyaluronic acid also facilitates proliferation, migration, and extracellular matrix production by various cell types, including vascular endothelial and smooth muscle cells. (Leach J B et al., *Encyclopedia of Biomaterials and Biomedical Engineering* Wnek G E et al., Eds. (Marcel Dekker, New York, 2004) pp. 779-789).

Advantageously, hyaluronic acid has low immunogenicity and non-thrombogenic properties as distinguished from other molecules that induce wound healing. For example, collagen is highly thrombogenic and unsuitable for intravascular use.

Hyaluronic acid is a member of the polysaccharide family of compounds, specifically the GAG family. GAGs (also referred to as mucopolysaccharides) are long unbranched polysaccharides having repeating disaccharide units, which contains an N-acetyl-hexosamine and hexose (or hexuronic acid). The combination of the sulfate group and the carboxylate groups of the uronic acid residue provides a high negative density charge. Members of the GAG family of compounds include hyaluronic acid, heparin, dermatan sulfate, chondroitin sulfate and others. Heparin is generally described in Linhardt R J et al., "Isolation and characterization of human heparin," *Biochemistry* 1992, 31(49):12441-12445.

Polyurethane (PU) polymers are characterized by a chain of organic units joined by urethane linkages. Polyurethanes are commonly made by reacting a diisocyanate (aromatic or aliphatic) and a polyol (such as a polyether polyol, like polyethylene glycol, or a polyester polyol). An exemplary polyol is 1,4-butanediol. An exemplary diisocyanate is the reaction product of 4,4'-methylene-di(p-phenyl isocyanate) and poly (tetramethylene oxide)$_n$, whereby n=10 to 40.

Polyurethane may be fabricated using a wide variety of processing technologies, such as casting, electrostatic and wet fiber/monofilament spinning, extrusion, dip coating, and spraying.

An exemplary embodiment of the invention is directed to a bioactive and biocompatible PU-diol-GAG salt copolymers, specifically polyurethane-butanediol-hyaluronic acid salt (PUBD-HA) copolymers, for use in medical implant devices. The biocompatible urethane component being the reaction product of 4,4'-methylene-di-(p-phenyl isocyanate) and poly (tetramethylene oxide), and further reacted with 1,4-butanediol, wherein n=10 to 40.

In another exemplary embodiment, the bioactive GAG is a salt of hyaluronic acid, such as a cetylpyridinium salt acid having 5 to 10,000 repeating units or a dimethyldioctadecylammonium salt of heparin has 5 to 65 repeating units. The weight content of GAG (i.e., the cetylpyridinium salt or the dimethyldioctadecylammonium salt) is an amount sufficient to render the copolymer bioactive. Preferably, the weight content of the polyurethane-diol is an amount sufficient to render the copolymer sufficiently flexible and rigid for endovascular delivery into a vascular aneurysm and for use as a polymeric shell, having coiled NiTi component disposed therein, within the vascular aneurysm.

In general, preferred uses of the invention is synthesis of an elastic, compliant polymer shell that induces suitable wound healing responses, such as the bioactive spherical aneurysm occlusion device shown in the related patent application set forth herein. Preferably, the polymer shell is also hemocompatible. The polymer combines the elasticity and mechanical strength of polyurethane with the bioactivity of hyaluronic acid.

Along with the materials described above for construction of the biocompatible polymeric member into which the metallic frame member or liquid embolic agent may be introduced, there are additional materials that are suitable for construction of the polymeric member. Some other suitable materials include, for example, polyester materials, silicone-based materials and derivatives thereof, polyethylene materials including polytetrafluoroethylene, biocompatible urethanes and derivatives thereof, and other biocompatible polymers.

Figure 7:
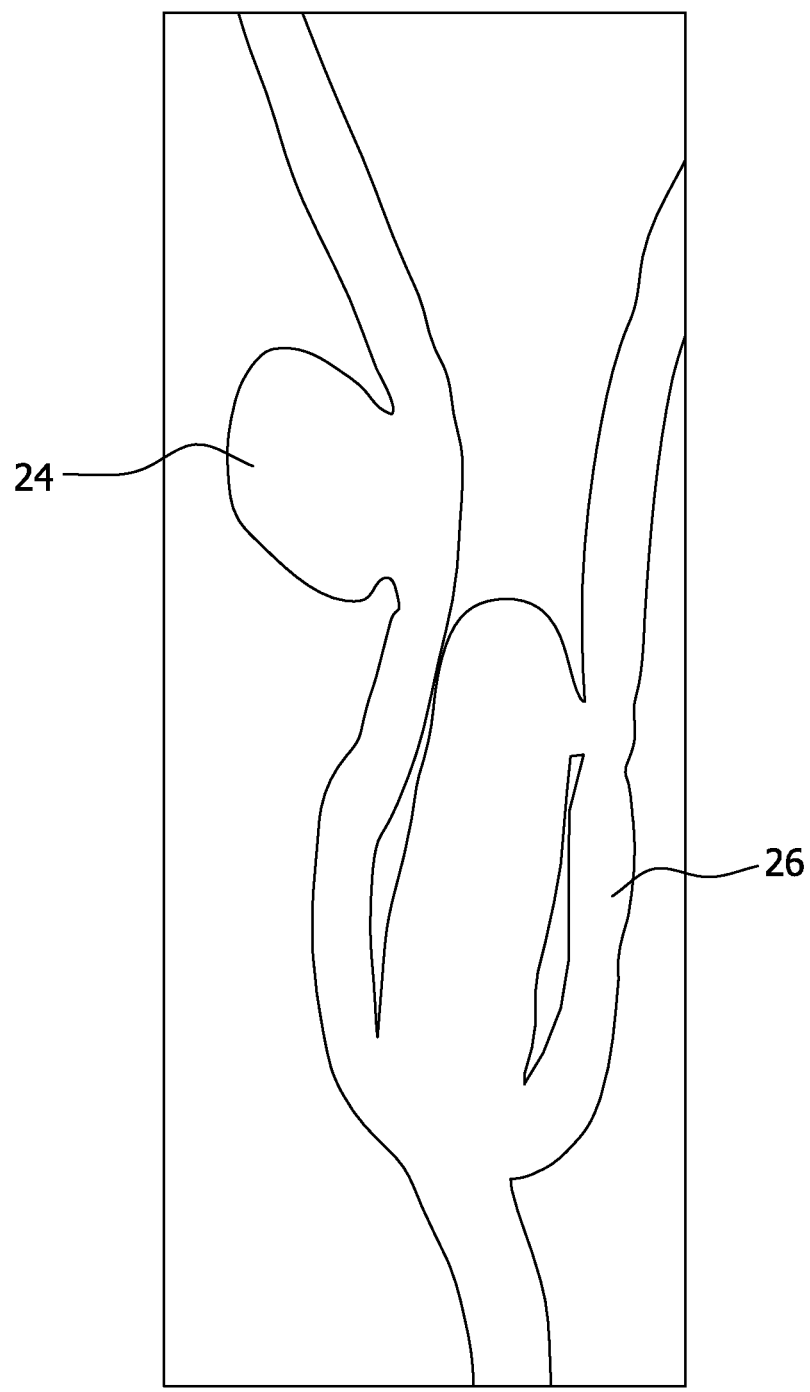
FIG. 7 shows two aneurysms of different morphologies and sizes having sidewall and bifurcation aneurysms, whereby angiography of the smaller side-wall aneurysm and larger bifurcation aneurysm in a canine is shown.

Shown in FIG. 7 are two aneurysms 24, 26 of different morphologies and sizes having sidewall and bifurcation aneurysms. Angiography of the smaller side-wall aneurysm 24 and larger bifurcation aneurysm 26 in a canine shown occlusion of the aneurysms using the instant invention.

Preferably, the polymeric shell is also hemocompatible. The copolymer combines the elasticity and mechanical strength of polyurethane with the bioactivity of hyaluronic acid.

Figure 8:
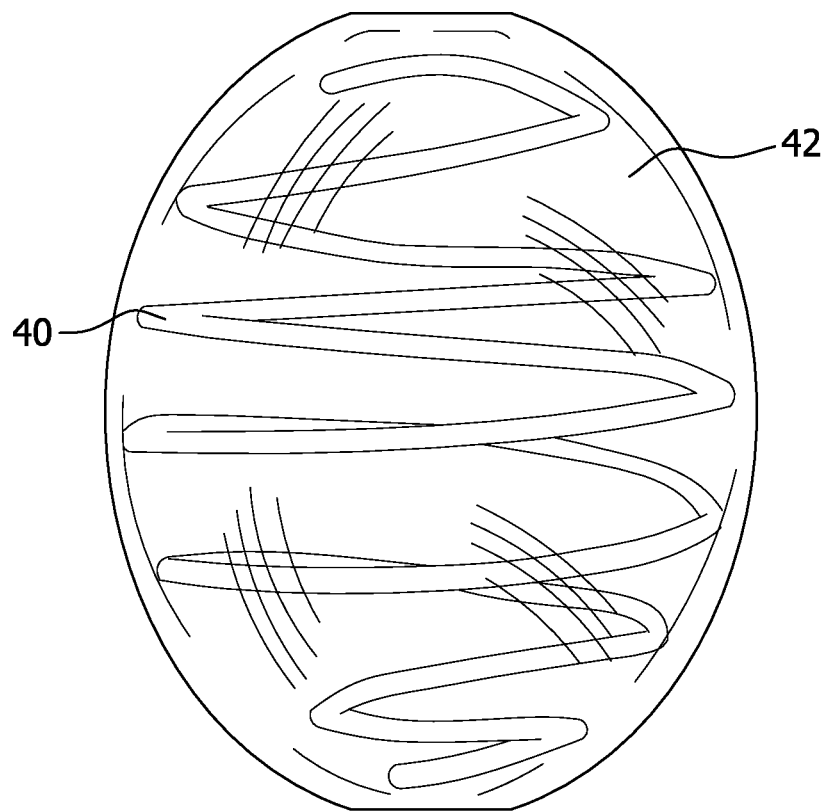
FIG. 8 shows a perspective view of another embodiment of the endovascular aneurysm occlusion medical device of the invention.
Figure 9:
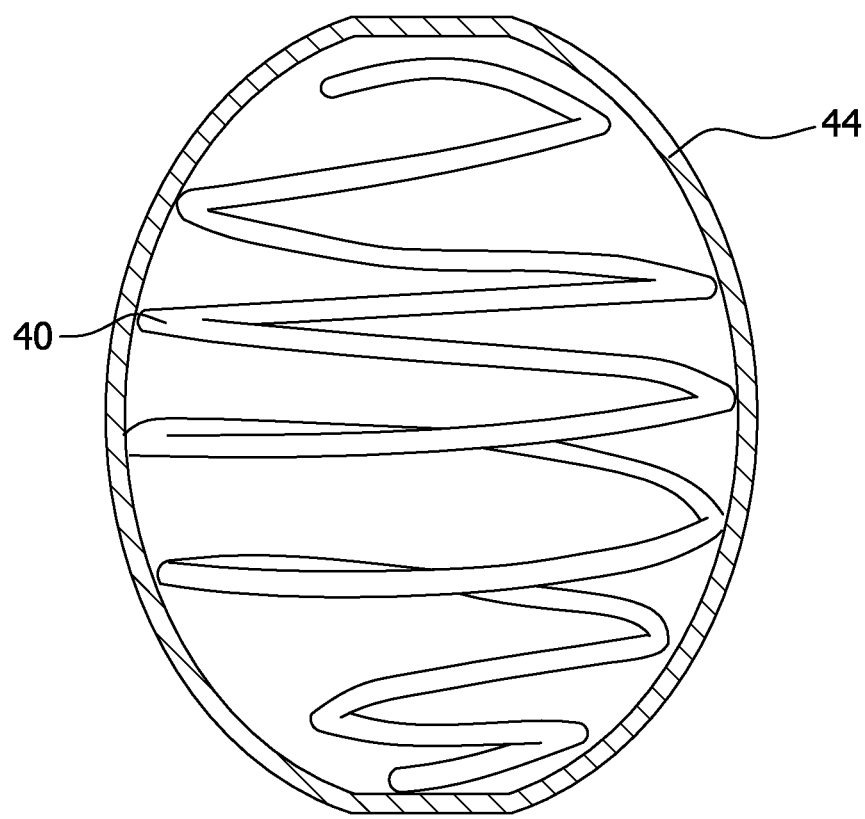
FIG. 9 shows a cross-sectional view of the embodiment shown in FIG. 8.

Shown in FIGS. 8 and 9 is another embodiment of the endovascular aneurysm occlusion medical device of the invention including a hemocompatible polymeric shell 42 structurally supported by a biocompatible metallic frame 40. The wall 44 of the shell 44 is shown in a cross-sectional view.

Figure 10:
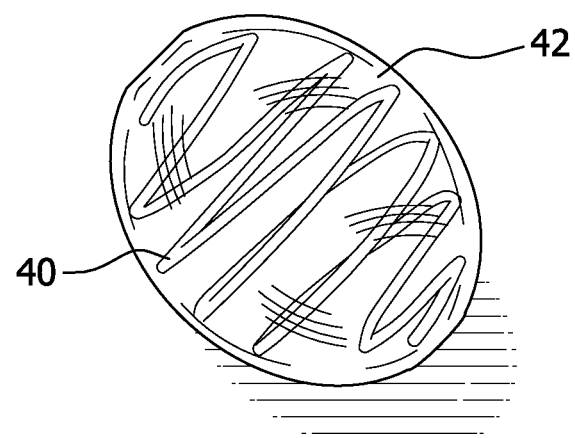
FIG. 10 shows a photograph of a wire frame in a polymeric shell in accordance with one embodiment described herein.

Shown in FIG. 10 is an endovascular aneurysm occlusion medical device of the invention including a hemocompatible polymeric shell 42 and a biocompatible metallic frame 40.

As noted above, in an alternative embodiment of the present disclosure, the endovascular aneurysm occlusion device includes the polymeric member as described hereinabove as well as a liquid embolic agent that is capable of solidifying upon ejection from the occlusion device and into the polymeric member; that is, once the liquid embolic agent is injected into the polymeric member and inflates it inside of the aneurysm, it solidifies therein upon activation and initiates a cascade of wound healing events. In accordance with the present teachings, the liquid embolic agent that ultimately solidifies inside of the polymeric member may be a one component liquid embolic agent, or may be a liquid embolic agent that includes a first component and a second component (and possibly a third component, a fourth component, etc.); that is, the liquid embolic agent injected into the polymeric material may be one single solution (a one component liquid embolic agent) capable of solidifying in the polymeric material upon activation, or it may be a combination of two or more components that, upon mixing and/or activation within the polymeric material inside of the aneurysm, solidify.

As would be recognized by one skilled in the art based on the disclosure herein, when a liquid embolic agent including two or more components is utilized, the occlusion device is generally configured to hold the two liquids separate until ejection therefrom into the polymeric material at which time they are mixed or contacted together. In one suitable embodiment where a two component liquid embolic agent is utilized and the two components are held separate until injection into the polymeric material, a double channel or double lumen catheter is utilized. The double channel or double lumen catheter is configured to hold two liquids separate until ejection therefrom and into the polymeric material where they can contact and thoroughly mix together. In an alternative embodiment, when a liquid embolic agent including a first component and a second component is used, the first component and second component may be mixed together prior to delivery or may be introduced in sequence.

Suitable liquid embolic agents include those liquids that can be safely utilized inside of the human body and which can solidify upon activation inside of a polymeric member as described herein. Suitable liquid embolic agents that can solidify upon activation without mixing with another liquid (i.e., single component liquid embolic agents) include cyanoacrylate solutions, polyvinyl alcohol solutions, ethylene vinyl copolymer solutions, cellulose acetate solution, polymethylmethacrylate solutions, polyvinyl acetate solutions, hydrogel solutions, polyurethane solutions, poly(ethylene glycol) solutions, polyester solutions, polyhydroxyethyl methacrylate solutions, polyanhydride solutions, silicone solutions, polysilane solutions and combinations and copolymers thereof. Suitable liquid embolic agents that can solidify upon the mixing of two liquid agents (i.e., a two component or more liquid embolic agent) include a calcium solution used in combination with an alginate solution and a sodium solution used in combination with an alginate solution, and a solution containing a divalent cation and an alginate solution. As noted above, when the liquid embolic agent includes two or more components are utilized and mixed to solidify inside of the polymeric member, they may be held separately until mixed together inside of the polymeric member.

The viscosity of the component(s) of the liquid embolic agent to be injected into the polymeric member inside of the aneurysm is not generally critical and need only be such that it can be pumped out of the injection device, such as a catheter or double lumen catheter, under physiological conditions. Stated another way, the viscosity of the component(s) that make up the liquid embolic agent prior to solidification inside of the polymeric shell should be such that it is suitable for easy injection during a procedure for occluding an aneurysm.

As previously mentioned, the liquid embolic agent is caused to solidify inside of the polymeric member through the use of an activation means. Any safe, suitable activation means that can induce solidification of the liquid embolic agent inside of the polymeric member may be utilized. Specific examples of safe, suitable activation means include exposure to ultraviolet radiation, mixing of two liquid solutions, agitation, exposure to ultrasonic energy, heating, and combinations thereof.

Once the liquid embolic agent has been injected into the polymeric member inside of the aneurysm and allowed to solidify, it is of sufficient strength and density such that it can withstand the pressure or external force placed upon it by the blood (blood pressure) without substantially deforming, collapsing, or breaking apart. Although the exact level or hardness or denseness provided by the solidified liquid embolic agent inside of the polymeric member is not critical, it should be of sufficient strength such that the pressure supplied against it by the blood does not cause the polymeric member to lose effectiveness.

In one optional embodiment of the present invention, the polymeric shell into which the liquid embolic agent is injected can be coated on the inside surface prior to usage with a contrast agent. The contrast agent can be easily viewed utilizing X-rays or comparable visualization techniques during the procedure to place the polymeric shell and liquid embolic (or polymeric shell and biocompatible metallic frame member) into the aneurysm. By increasing the visibility of the polymeric shell during insertion, the preciseness and accuracy of the placement of the polymeric shell and ultimately the liquid embolic agent or biocompatible frame member can be improved. Any biocompatible contrast agent can be used in accordance with the present invention. One specific contrast agent suitable for use on the inside surface of the polymeric shell is a tantalum powder.

In another optional embodiment of the present invention, a contrast agent can be directly introduced and dissolved into the liquid embolic agent prior to injection into the polymer shell material. For example, if an alginate solution is used as a liquid embolic agent, a contrast agent, such as a tantalum powder, can be mixed with the alginate powder and then the mixture introduced into water and dissolved. Upon usage and injection into the polymeric shell material, the tantalum will be visible using X-rays or comparable visualization techniques. In one embodiment, 25 wt % tantalum powder, 2 wt % alginate powder, and 73 wt % water are mixed together and used as the alginate solution for injection into the polymeric material. As would be recognized by one skilled in the art based on the disclosure herein, the tantalum powder could be mixed with a calcium or sodium solution that is commonly used in combination with an alginate solution when the liquid embolic agent is comprised of two separate liquids held apart until injection into the polymeric material.

The endovascular aneurysm occlusion devices as described herein can be utilized in various methods to occlude aneurysms in accordance with the present disclosure. In one particular embodiment, an elastic hemocompatible member (polymeric member) defining an interior chamber is first endovascularly disposed into a vascular aneurysm utilizing the device. After the hemocompatible member is in the aneurysm, the device ejects a liquid embolic agent (or combination of liquid embolic agents) into the hemocompatible member to inflate the member within the aneurysm. Once inside of the hemocompatible member, the liquid embolic agent is activated and caused to solidify therein and occlude the aneurysm.

In another embodiment of the present invention, a combination of a liquid embolic agent (single or multiple component) and a biocompatible metallic frame member may be introduced into a polymeric member inside of an aneurysm; that is, both a biocompatible metallic frame member and a liquid embolic agent are introduced into the polymeric member and the liquid embolic agent is allowed to solidify inside of the polymeric member freezing in place the biocompatible metallic frame member. This combination of the biocompatible metallic frame member and the liquid embolic agent may provide superior structural support of the polymeric member and substantially resist compaction and degradation. With this embodiment, when a single component liquid embolic agent is used, it is generally desirable to first introduce the biocompatible frame member into the polymeric member and then subsequently introduce the single component liquid embolic agent into the polymeric member to ensure that the single component liquid embolic agent does not begin to solidify before the biocompatible frame member is present.

EXAMPLES

Example 1

Figure 5:
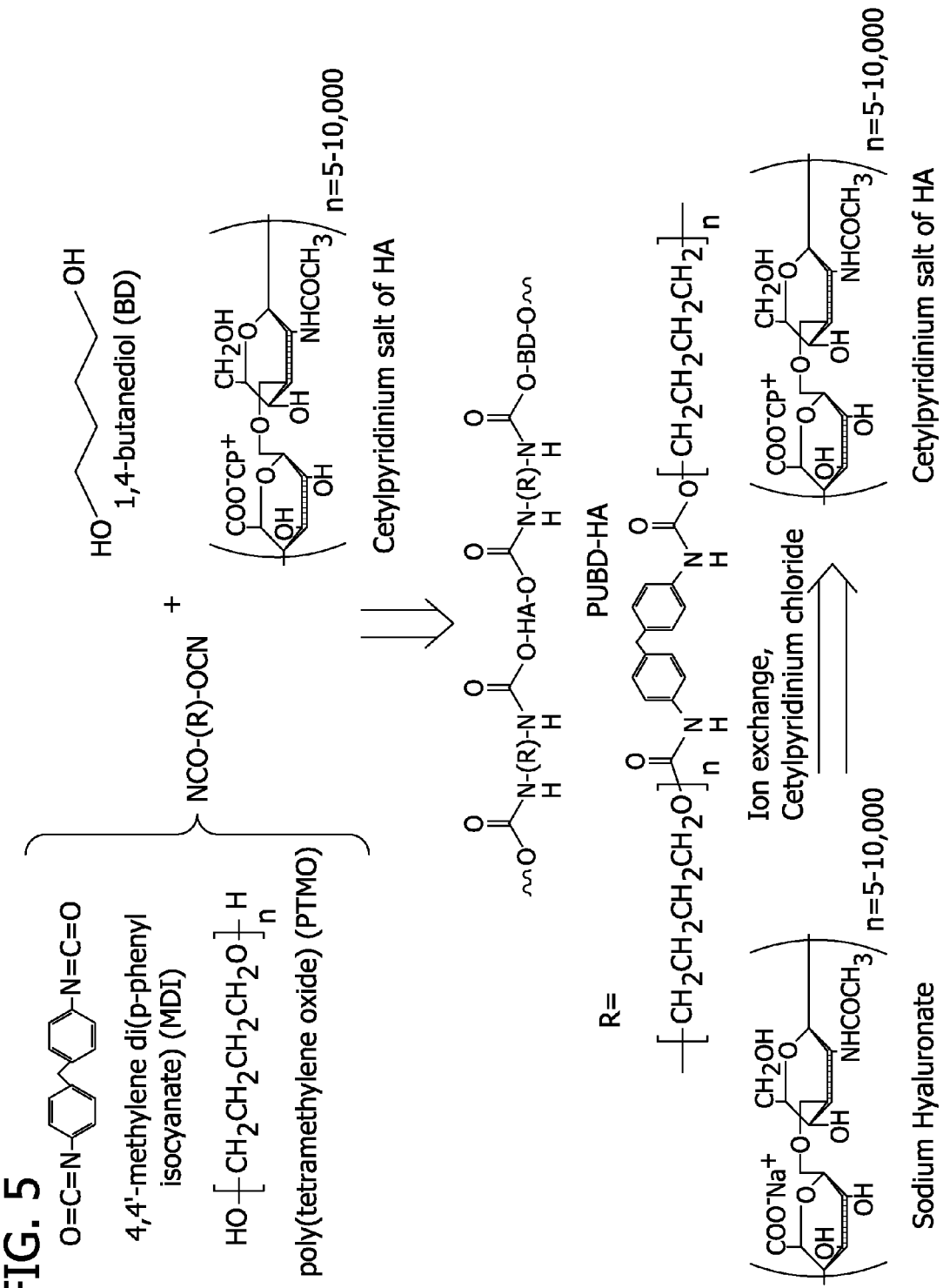
FIG. 5 shows the synthesis of the PUBD-HA copolymer and synthesis of the DMF-soluble HA salt.

As shown in FIG. 5, a polyurethane prepolymer is synthesized and reacted with the cetylpyridinium salt of hyaluronic acid to make the PUBD-HA copolymer. Thin, transparent films of PUBD are synthesized by solvent casting, whereby the films possess excellent mechanical strength (5.3-11 MPa elastic modulus) and elasticity (>1000% elongation). The biocompatibility and bioactivity of PUBD-HA is confirmed using in vitro cell culture tests. Endothelial cells and fibroblasts are cultured upon PUBD-HA or PUBD for time periods up to 5 days. Using conventional assays, the cultures are used to assess cell viability and number.

Hyaluronic Acid Degradation. Native hyaluronic acid has a very high molecular weight (~4 MDa). Hyaluronic acid that is lower in molecular weight is easier to handle (with respect to dissolution), and it stimulates endothelialization and wound healing. The following steps were taken to partially degrade hyaluronic acid creating low molecular weight hyaluronic acid.

Starting materials include hyaluronic acid sodium salt having MW=4 MDa (Fluka) and hyaluronidase (from bovine testes, 1040 U/ml, Sigma) were procured.

Methods. A 5 mg/ml solution of hyaluronic acid in 20 ml diH$_2$O was prepared in a 50 ml centrifuge tube. Hyaluronidase (HyAse) was added to the hyaluronic acid-containing aqueous solution producing a HyAse concentration of 500 U/ml. The solution was incubated in a 37° C. water bath overnight, and then it was heated in a 70° C. water bath for 30 minutes to inactivate the HyAse. After cooling to room temperature, 2 ml of the degraded hyaluronic acid solution was transferred to a 15 ml centrifuge tube for ion exchange with cetylpyridinium chloride (CPC). The degraded hyaluronic had MW=9300.

Synthesis of HA-CPC. Hyaluronic acid and the degradation products are soluble in H$_2$O. Synthesis of polyurethane-hyaluronic acid copolymers (PU-HA) involves dissolving hyaluronic acid in organic solvent(s) such as dimethyl formamide (DMF) or tetrahydrofuran (THF). The following method describes a simple ion exchange reaction that replaces the sodium salt of hyaluronic acid with a cetylpyridinium salt of hyaluronic acid, whereby the latter is soluble in DMF.

Starting materials include un-degraded or degraded hyaluronic acid (of any molecular weight), cetylpyridinium chloride (Sigma) and anhydrous N,N-dimethylformamide (DMF) (Aldrich).

Methods. A 0.48% (w/v) solution of CPC in 2 ml diH$_2$O was added dropwise to 2 ml of hyaluronic acid solution forming a white precipitate. The precipitate was separated from the solution by centrifugation. After removing the supernatant, the precipitate was washed using 2 ml diH$_2$O and centrifuged, whereby the supernatant was removed again. The precipitate was frozen and dried overnight. The end-product was HA-CPC powder having approximately 25 HA repeating units.

Synthesis of PUBD-HA. Synthesizing a copolymer of polyurethane-butanediol and hyaluronic acid. Starting materials include methylene di(p-phenyl isocyanate) (MDI)(Aldrich), poly(tetramethylene oxide) (PTMO) having n=14 and Mn=1000 (Aldrich), 1,4-butanediol (BD), anhydrous N,N-dimethylformamide (DMF)(Aldrich), and HA-CPC powder.

Methods. A 10% (w/v) solution of MDI (2 mmol; MW=250) in 5 ml of DMF was prepared in a 100 ml round-bottom flask and stirred at room temperature. A 10% (w/v) solution of PTMO (1 mmol; MW=1000) in 10 ml of anhydrous DMF was added. The mixture was heated to 90° C. and maintained at that temperature for 3 h under argon. The reactor was cooled to room temperature. BD (0.9 mmol; MW=90) in 2 mL of anhydrous DMF was added. The HA-CPC powder was dissolved in 4 ml anhydrous DMF and warmed to 50° C. The HA-CPC solution in DMF was added to the reactor and incubated at 50° C. for 3 h under argon. The polymer solution was cooled to room temperature, precipitated in methanol, and dried naturally in a hood. The end-product was the copolymer PUBD-HA shown in FIG. 5.

Five PUBD-HA copolymers were synthesized, whereby the weight % content of hyaluronic acid was 0.33%, 0.66%, 1.33%, 2% and 5.4%. The content of each copolymer was verified using 1H NMR for incorporation of hyaluronic acid into the polyurethane backbone.

Films of PUBD-HA were created by dissolving suitable amounts of copolymer with DMF in a Teflon evaporation dish. The solvent was allowed to evaporate leaving polymer films of ~200 μm thickness. These films can be sterilized using ethanol, UV exposure, or EtO treatment.

The instant compositions are not enzymatically degradable by hyaluronidase. Theoretically, at elevated hyaluronic acid content levels, the PUBD-HA copolymers may become enzymatically degradable.

Results and Contact Angle. The contact angle of diH$_2$O on a copolymer film decreased with increasing hyaluronic acid content ($p<0.01$ by one-way ANOVA), which indicates increased hydrophilicity with increased hyaluronic acid content. *$p<0.03$ compared to PUBD by two-tailed t-test.

Mechanical Properties. With the exception of copolymer containing 0.33% hyaluronic acid, no significant change was observed in tensile strength. Elastic modulus significantly increased with increasing hyaluronic acid content ($p<0.001$ by one-way ANOVA). *$p<0.001$ compared to PUBD by two-tailed t-test.

Fibroblast Adhesion and Proliferation. Increased hyaluronic acid content resulted in decreased adhesion. It also resulted in decreased proliferation of NIH 3T3 fibroblasts cultured on PUBD-HA films ($p<0.001$ by one-way ANOVA for both time points), which may change depending upon molecular weight of hyaluronic acid and cell type. The PUBD-HA copolymer may inherently inhibit cell adhesion and proliferation. The MW of the tested hyaluronic acid inhibited the proliferation of fibroblasts. Other experiments will determine whether endothelial cells behave in a similar manner.

Example 2

Starting materials include heparin sodium salt having MW=16,000 (Sigma).

Synthesis of Hep-DDA. Heparin is soluble in $H_2O$ Synthesis of polyurethane-heparin copolymers (PU-Hep) involves dissolving heparin in organic solvent(s) such as dimethyl formamide (DMF) or tetrahydrofuran (THF). The following method describes a simple ion exchange reaction that replaces the sodium salt of heparin with a dimethyldioctadecylammonium salt of heparin, whereby the latter is soluble in DMF.

Starting materials include un-degraded and degraded heparin (of any molecular weight), dimethyldioctadecylammonium chloride (DDAC) (Fluka) and anhydrous N,N-dimethylformamide (DMF)(Aldrich).

Methods. A 0.48% (w/v) solution of DDAC in 2 ml di$H_2O$ was added dropwise to 2 ml of sodium heparin solution, forming a white precipitate. The precipitate was separated from the solution by centrifugation. After removing the supernatant, the precipitate was washed using 2 ml di$H_2O$ and centrifuged, whereby the supernatant was removed again. The precipitate was frozen and dried overnight. The end-product was Hep-DDA powder having approximately 27 Hep repeating units.

Synthesis of PUBD-Hep. Synthesizing a copolymer of polyurethane-butanediol and heparin. Starting materials include methylene di(p-phenyl isocyanate) (MDI)(Aldrich), poly(tetramethylene oxide) (PTMO) having n=14 and Mn=1000 (Aldrich), 1,4-butanediol (BD), anhydrous N,N-dimethylformamide (DMF)(Aldrich), and Hep-DDA powder.

Figure 6:
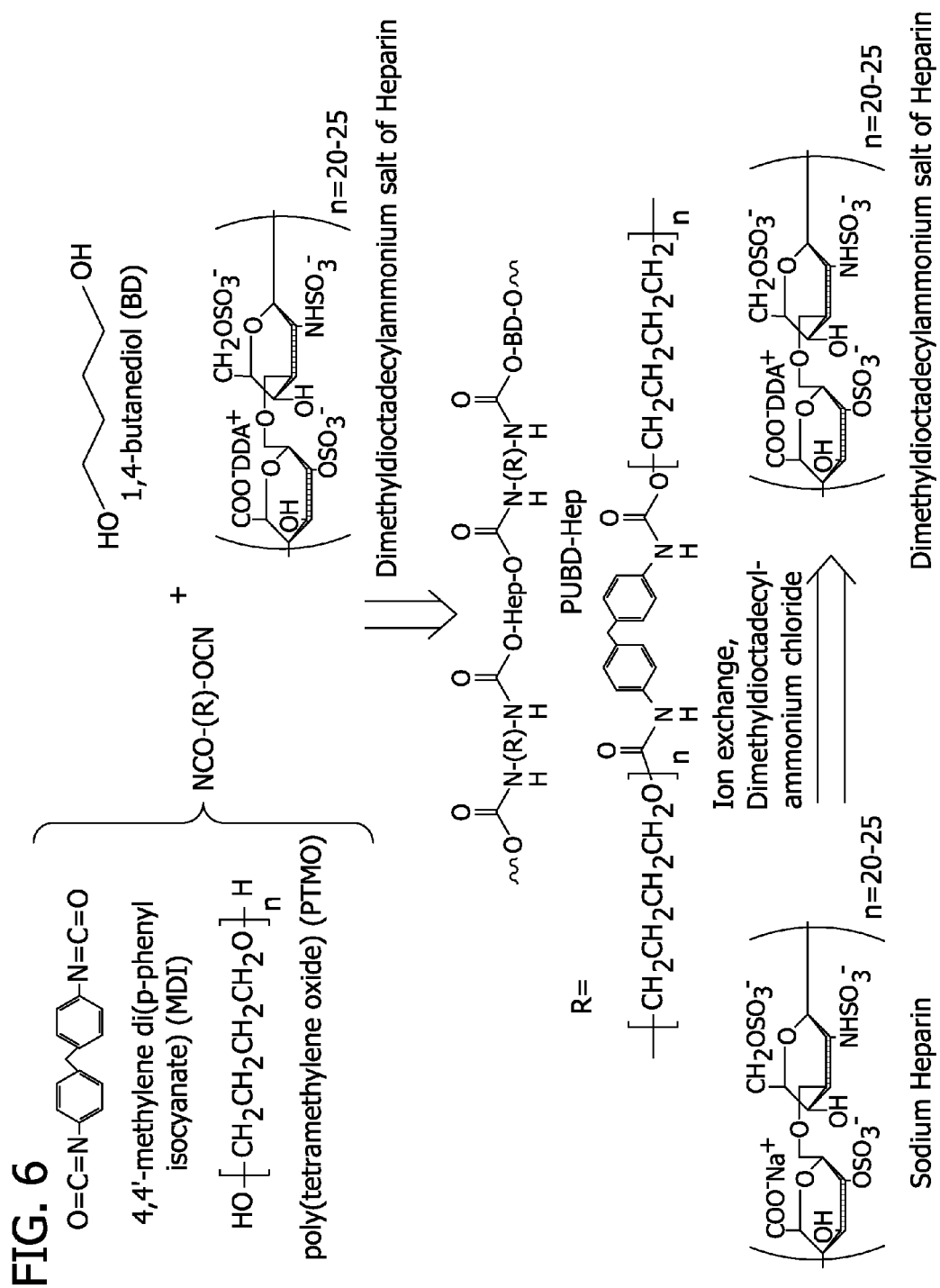
FIG. 6 shows the synthesis of PUBD-heparin copolymer and synthesis of the DMF-soluble heparin salt.

Methods. A 10% (w/v) solution of MDI (2 mmol; MW=250) in 5 ml of DMF was prepared in a 100 ml round-bottom flask and stirred at room temperature. A 10% (w/v) solution of PTMO (1 mmol; MW=1000) in 10 ml of anhydrous DMF was added. The mixture was heated to 90° C. and maintained at that temperature for 3 h under argon. The reactor was cooled to room temperature. BD (0.9 mmol; MW=90) in 2 mL of anhydrous DMF was added. The Hep-DDA powder was dissolved in 4 ml anhydrous DMF and warmed to 50° C. The Hep-DDA solution in DMF was added to the reactor and incubated at 50° C. for 3 h under argon. The polymer solution was cooled to room temperature, precipitated in methanol, and dried naturally in a hood. The end-product was the copolymer PUBD-Hep shown in FIG. 6.

Two PUBD-Hep copolymers were synthesized, whereby the weight % content of heparin was 0.66% and 1.33%.

Films of PUBD-Hep were created by dissolving suitable amounts of copolymer with DMF in a Teflon evaporation dish. The solvent was allowed to evaporate leaving polymer films of ~200 μm thickness. These films can be sterilized using ethanol, UV exposure, or EtO treatment.

Example 3

In this Example, aneurysm occlusion was tested using a model aneurysm system in which an occlusion mechanism was inserted. The mechanism was either: (1) a biocompatible metallic frame member inserted into a polymeric member; or (2) a liquid embolic agent injected into a polymeric material and allowed to solidify. Once the polymeric member including either the biocompatible frame member or the liquid embolic agent was introduced into the aneurysm model, the amount of occlusion was determined.

In vitro models of aneurysms were prepared using a silicone polymeric system (See, Schmitz-Rode T, et al., Invest Radiol, 1999, 34(4): 317-321). Aneurysm models were prepared for testing having neck sizes that range from small (4.5 millimeters) to medium (5.5 millimeters) to large (7 millimeters). Each of the three sizes was tested at three different vascular flow rates: 49 mL/min, 116 mL/min, and 208 mL/min. The fluid used to create the desired vascular flow rates was a fluid with a similar viscosity to blood. Control testing conditions consisted of model aneurysms of the same neck sizes with no occlusion device that was exposed to the desired flow rate. The biocompatible metallic frame member was a NiTi metal memory component as described herein and the liquid embolic agent utilized was a sodium alginate solution as described herein. Either the metallic frame member or the sodium alginate solution was introduced into a polymeric shell material. The device was then inserted into the model aneurysm prior to flow testing. Aneurysm occlusion was tested by analyzing whether any fluid leaked into the aneurysm. For both the polymeric material including the metallic frame member and the liquid embolic agent, complete occlusion of the model aneurysm could be obtained.

Example 4

In this example, the device consisted of a single NiTi component within an elastic, biocompatible polymer shell, made of a polyurethane-hyaluronic acid copolymer. The outer polymeric shell and inner NiTi component coil were created separately and then assembled, and devices were sized to be 6-12 mm in diameter. For the purposes of evaluating device performance, the devices were constructed and delivered in their final configuration (fully-deployed coil within the expanded shell).

The NiTi coil was made of 0.0100" component and formed into helical coils with diameters of 6, 8, 10, and 12 mm. The component was fixed on a special spherical stainless steel jig of the appropriate diameter. The jigs were created by drilling and tapping a hole through the center of the sphere and the bolt threaded into this hole was used to hold the NiTi component on the outside of the sphere during the process of creating a grooved pattern via electrical discharge machining. The bolt was then used to clamp the ends of the NiTi component with a set of nuts and maintain the component in the helical trough during heat treatment. Heat-treatment of the component was conducted while fixed on the jig and was performed in a tube furnace at 550° C. for 35 minutes while argon was passed through the furnace to minimize oxidation. Following the treatment, the coils were allowed to slowly cool, in air, for at least 30 minutes.

A copolymer of hyaluronic acid (HA) with polyurethane (PU) was synthesized for the shell material. Ion exchange with cetylpyridinium chloride was used to create the cetylpyridinium salt of HA from HA sodium salt. The HA was combined with a polyurethane prepolymer synthesized from a 2:1 molar ratio of methylene di(p-phenyl isocyanate) and poly(tetramethylene oxide) and reacted at 50° C. for 3 h under argon. This synthesis yielded a copolymer of PU with HA. The PU-HA copolymer was dissolved in dimethylformamide at a concentration of 40 mg/ml. Films of PU-HA were solvent-casted onto cylindrical PTFE molds of different diameters and lengths by dipping the cylinders into the PU-HA polymer solution followed by drying on a rotating platform. Hemispherical films of PU-HA (~50 □m in thickness) were created in this manner.

A complete device was constructed using a NiTi coil and two PU-HA hemispherical films of matching diameter. The NiTi coil was placed within two PU-HA hemispherical films and the seams of the films were joined via application of PU-HA polymer solution, which bound the hemispheres together upon drying.

In one swine under general anesthesia, sacculus-like lateral side-wall aneurysms were created surgically by anastomosing a vein pouch to the common carotid artery. This aneurysm model was first described by the University of Wisconsin endovascular laboratory in the Department of Radiology and has been used in testing aneurysm occlusion devices for the last 18 years. The porcine animal model was used to study acute, short-term, occlusion efficacy.

The swine was anesthetized and intubated and ventilated. Under temporary carotid occlusion, a section of jugular vein was removed and sutured to the carotid artery at a right angle, making an aneurysm pouch. Devices were inserted from the top of the aneurysm pouch, and pouches closed using sutures. Carotid blood flow was restored, and angiography was performed immediately post-implantation to assess the success of the aneurysm occlusion. The device successfully occluded the aneurysm, preventing blood flow into the aneurysm sack and maintaining patency of the parent vessel.

Example 5

In this example, the device consisted of a biocompatible polymer shell, made of a polyurethane-hyaluronic acid copolymer, filled with an alginate gel. The outer polymeric shell was created first and then the gel was injected at a quantity adequate to occlude the aneurysm. For the purposes of evaluating device performance, the devices were not delivered endovascularly.

A copolymer of hyaluronic acid (HA) with polyurethane (PU) was synthesized for the shell material. Ion exchange with cetylpyridinium chloride was used to create the cetylpyridinium salt of HA from HA sodium salt. The HA was combined with a polyurethane prepolymer synthesized from a 2:1 molar ratio of methylene di(p-phenyl isocyanate) and poly(tetramethylene oxide) and reacted at 50° C. for 3 h under argon. This synthesis yielded a copolymer of PU with HA. The PU-HA copolymer was dissolved in dimethylformamide at a concentration of 40 mg/ml. Films of PU-HA were solvent-casted onto cylindrical PTFE molds of different diameters and lengths by dipping the cylinders into the PU-HA polymer solution followed by drying on a rotating platform. Hemispherical films of PU-HA (~50 µm in thickness) were created in this manner. A complete shell was constructed using two PU-HA hemispherical films of matching diameter. The seams of the films were joined via application of PU-HA polymer solution, which bound the hemispheres together upon drying.

The components needed for alginate gelation were prepared prior to the in vivo procedure and final mixing of the components was conducted during the in vivo study. The alginate gelation procedure is a modification of that described in Kuo C. K., Ma P. X. (2001) "Ionically crosslinked alginate hydrogels as scaffolds for tissue engineering: Part 1. Structure, gelation rate and mechanical properties." Biomaterials, 22:511-521. A 2 weight % sodium alginate solution was created in a 1:1 by volume mixture of Omnipaque™ and sterile deionized $H_2O$ (Component A). A separate solution suspending 486.4 mg of $CaCO_3$ in 92 ml sterile deionized $H_2O$ was created (Component B). Additionally, 0.866 g of D-glucono-γ-lactone (GDL) was dissolved in 20 ml of sterile deionized $H_2O$ (Component C). The three components described above where mixed in the following manner. Using a syringe, 2 ml of Component A was placed in a sterile 5 ml centrifuge tube, followed by the addition of 0.92 ml of Component B. These components in the centrifuge tube were vortexed to make a homogeneous suspension (Component D). Using a 26# syringe needle, 0.02 ml of Component C was drawn into a 3 ml syringe. Using the same syringe with a 20# syringe needle, the total volume of Component D was then drawn into the syringe. Mixing of these components is encouraged by movement of the plunger with the needle directed upwards. At this point, the gelation has been initiated, and the working time of this particular gel solution is roughly 15 minutes. The syringe needle is then changed back to a 26# needle. This small gauge needle is used to pierce the PU-HA shell with minimal disruption of the shell integrity. Air is removed from the interior of the shell by compressing it, and the gel mixture is injected into the shell. Multiple injections of the gel can be accomplished to create the appropriate filling of the device during the 15 minute time window.

In one canine under general anesthesia, sacculus-like lateral side-wall aneurysms were created surgically by anastomosing a vein pouch to the common carotid artery. This aneurysm model was first described by the University of Wisconsin endovascular laboratory in the Department of Radiology and has been used in testing aneurysm occlusion devices for the last 18 years. The canine was anesthetized and intubated and ventilated. Under temporary carotid occlusion, a section of jugular vein was removed and sutured to the carotid artery at a right angle, making an aneurysm pouch. The device shell with a small amount of gel was inserted from the top of the aneurysm pouch. Additional gel material was injected into the shell after insertion into the pouch and the pouch was closed using sutures. Carotid blood flow was restored, and angiography was performed immediately post-implantation to assess the success of the aneurysm occlusion. The device successfully occluded the aneurysm, preventing blood flow into the aneurysm sack and maintaining patency of the parent vessel.

We claim:
1. An endovascular medical device comprising:
a polymeric member defining an interior chamber, wherein the polymeric member is constructed from a copolymer comprising a biocompatible polyurethane and a bioactive polysaccharide, wherein the bioactive polysaccharide is incorporated into the biocompatible polyurethane backbone of the copolymer; and
a biocompatible metallic frame member comprising one or more components constructed from a NiTi alloy having a transformation temperature below a patient's body temperature, disposed within the interior chamber, and adapted to structurally support the polymeric member.
2. The medical device of claim 1, wherein the bioactive polysaccharide is a bioactive glycosaminoglycan.

3. The medical device of claim 2, wherein the bioactive glycosaminoglycan is a member selected from the group consisting of a suitable salt of hyaluronic acid and a suitable salt of heparin.

4. The medical device of claim 3, wherein the salt of hyaluronic acid is a member selected from the group consisting of a cetylpyridinium salt and a tetrabutylammonium salt, and wherein the salt of heparin is a dimethyldioctadecylammonium salt.

5. The medical device of claims 4, wherein the salt of hyaluronic acid has 5 to 10,000 repeating units, and wherein the dimethyldioctadecylammonium salt of heparin has 5 to 65 repeating units.

6. The medical device of claim 1, wherein the weight content of the bioactive polysaccharide is in the range of about 0.05% to about 30%.

7. The medical device of claim 6, wherein the high and low range endpoints of the weight content of the bioactive polysaccharide are any combination of members selected from the group consisting of 0.05%, 0.1%, 0.33%, 0.66%, 1.3%, 2.0%, 5.4%, 10% and 30%.

8. The medical device of claim 7, comprising the cetylpyridinium salt of hyaluronic acid.

9. The medical device of claim 1, wherein the biocompatible urethane is the reaction product of 4,4'-methylene-di-(p-phenyl isocyanate) and poly(tetramethylene oxide)$_n$, and further reacted with 1,4-butanediol, and wherein n=10 to 40.

10. The medical device of claim 1, wherein the biocompatible urethane is the reaction product of 4,4'-methylene-di-(p-phenyl isocyanate) and poly(tetramethylene oxide)$_n$, and further reacted with 1,4-butanediol, and wherein n=10 to 40.

11. The medical device of claim 1, wherein the biocompatible urethane is the reaction product of a suitable isocyanate-containing molecule and a suitable poly($C_{2-10}$ alkylene oxide)$_n$, and further reacted with a suitable $C_{4-50}$ diol-containing molecule, wherein n=10 to 40, wherein the $C_{2-10}$ alkylene is linear or branched, substituted or un-substituted, and wherein the $C_{4-50}$ is linear or branched, substituted or un-substituted.

12. The medical device of claim 1, wherein the polymeric member has a wall thickness in the range of 0.05 to 0.4 mm.

13. The medical device of claim 12, wherein the polymeric member is adapted to substantially conform to a vascular aneurysm.

14. The medical device of claim 1, wherein the NiTi alloy comprises in the range of about 49 to about 51 wt. % Ni and in the range of about 51 to about 49 wt. % Ti.

15. The medical device of claim 14, wherein the metallic frame member comprises a single component.

16. The medical device of claim 14, wherein the metallic frame member is in the shape of a coil.

17. An endovascular medical device comprising:
a polymeric member defining an interior chamber and constructed from an elastic, hemocompatible polymer, wherein the elastic, hemocompatible polymer is modified with an anti-thrombotic agent and wherein the elastic, hemocompatible polymer is a member selected from the group consisting of poly(ethylene glycol), poly(vinyl alcohol), polytetrafluoroethylene, polyethylene terephthalate, poly(hydroxyethyl methacrylate), poly(hydroxyethyl acrylate), and a copolymer thereof, and,
a biocompatible metallic frame member comprising one or more components constructed from a NiTi alloy having a transformation temperature below a patient's body temperature, disposed within the interior chamber, and adapted to structurally support the polymeric member.

18. The medical device of claim 17, wherein the copolymer is a member selected from the group consisting of poly(ethylene glycol) diacrylate, poly(ethylene glycol) dimethacrylate and acrylated poly(vinyl alcohol).

19. The medical device of claim 17, wherein the anti-thrombotic modified derivative includes the hemocompatible polymer modified by an anti-thrombotic agent selected from the group consisting of heparin, chitosan and a nitric oxide donor molecule.

20. The medical device of claim 17, wherein the anti-thrombotic modified derivative is a member selected from the group consisting of heparin-releasing polyvinylpyrrolidone, heparin-releasing methacrylate, heparin-releasing polyester, nitric oxide-releasing polyester, and nitric oxide-releasing polyvinyl chloride.

21. The medical device of claim 17, wherein the polymeric member has a wall thickness in the range of 0.05 to 0.4 mm.

22. The medical device of claim 17, wherein the polymeric member is adapted to substantially conform to a vascular aneurysm.

23. The medical device of claim 17, wherein the alloy comprises in the range of about 49 to about 51 wt. % Ni and in the range of about 51 to about 49 wt. % Ti.

24. The medical device of claim 23, wherein the metallic frame member comprises a single component.

25. The medical device of claim 24, wherein the metallic frame member is in the shape of a coil.

* * * * *